United States Patent
Zang et al.

(10) Patent No.: US 8,703,500 B2
(45) Date of Patent: Apr. 22, 2014

(54) OPTOELECTRICAL VAPOR SENSING

(75) Inventors: Ling Zang, Salt Lake City, UT (US); Yanke Che, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 8 days.

(21) Appl. No.: 13/636,642

(22) PCT Filed: Mar. 23, 2011

(86) PCT No.: PCT/US2011/029652
§ 371 (c)(1),
(2), (4) Date: Nov. 21, 2012

(87) PCT Pub. No.: WO2011/119752
PCT Pub. Date: Sep. 29, 2011

(65) Prior Publication Data
US 2013/0183766 A1    Jul. 18, 2013

Related U.S. Application Data

(60) Provisional application No. 61/316,487, filed on Mar. 23, 2010.

(51) Int. Cl.
*G01N 27/26* (2006.01)
*G01N 27/00* (2006.01)
*G01N 27/414* (2006.01)
*B82B 1/00* (2006.01)
*B82Y 15/00* (2011.01)
*G01N 33/00* (2006.01)

(52) U.S. Cl.
CPC ............ *G01N 27/4146* (2013.01); *G01N 27/26* (2013.01); *G01N 27/4141* (2013.01); *B82B 1/00* (2013.01); *B82B 1/008* (2013.01); *B82Y 15/00* (2013.01); *G01N 33/0036* (2013.01)
USPC ............ 436/111; 436/96; 436/106; 436/136; 436/149; 436/151; 422/68.1; 422/82.01; 422/82.02; 422/88; 422/98

(58) Field of Classification Search
CPC . G01N 27/26; G01N 27/414; G01N 27/4141; G01N 27/4145; G01N 27/4146; G01N 33/0036; B82B 1/00; B82B 1/008; B82Y 15/00
USPC ........... 436/96, 106, 111, 112, 127, 136, 149, 436/151, 164, 167, 181; 422/68.1, 82.01, 422/82.02, 83, 88, 90, 98
See application file for complete search history.

(56) References Cited

U.S. PATENT DOCUMENTS 7,605,327 B2   10/2009   Roscheisen et al.
8,187,887 B2 *  5/2012   Swager et al. .................. 436/58
(Continued)

OTHER PUBLICATIONS

Yanke Che et al.; "Expedient Vapor Probing of Organic Amines Using Fluorescent Nanofibers Fabricated from an n-Type Organic Semiconductor"; Nano Letters, 2008, vol. 8, No. 8, pp. 2219-2223.

(Continued)

*Primary Examiner* — Maureen Wallenhorst
(74) *Attorney, Agent, or Firm* — Thorpe North & Western LLP

(57) ABSTRACT

A chemical sensor can include a nanofiber mass of p-type nanofibers having a HOMO level greater than −5.0 eV. Additionally, the chemical sensor can include oxygen in contact with the p-type nanofibers. Further, the chemical sensor can include a pair of electrodes in electrical contact across the nanofiber mass, where the p-type nanofibers conduct an electric current that decreases upon contact with an amine compound.

26 Claims, 11 Drawing Sheets

(56) References Cited

U.S. PATENT DOCUMENTS

| | | | |
|---|---|---|---|
| 8,486,708 B2* | 7/2013 | Zang et al. | 436/111 |
| 2005/0150778 A1 | 7/2005 | Lewis et al. | |
| 2009/0233374 A1 | 9/2009 | Zang et al. | |
| 2011/0171629 A1* | 7/2011 | Swager et al. | 435/5 |
| 2013/0126824 A1* | 5/2013 | Shih et al. | 257/9 |
| 2013/0302902 A1* | 11/2013 | Zang et al. | 436/111 |

OTHER PUBLICATIONS

Tammene Naddo, et al.; "Detection of Explosives with a Fluorescent Nonofibril Film"; Journal of the American Chemical Society, 2007, vol. 129, No. 22, pp. 6978-6979.

Ling Zang, et al.; One Dimensional Self-Assembly of Planar $\pi$ Conjugated Molecules: Adaptable Building Blocks for Organic Nanodevices ; Departments of Chemistry and Materials Science and Engineering, University of Illinois at Urbana—Champaign, Urbana, IL 61801.

Yanke Che, et al.; "Ambient Photodoping of p-Type Organic Nanofibers: Highly Efficient Photoswitching and Electrical Vapor Sensing of Amines"; Chem. Commun.; 2010, 46, 4127-4129.

PCT/US2001/029652; filed Mar. 23, 2010; University of Utah Research Foundation, et al.; international search report dated Dec. 28, 2011.

Naddo, et al.; "Highly responsive fluorescent sensing of explosives taggant with an organic nanofibril film"; Sensors and Actuators B: Chemical, 2008, vol. 134, Issue 1, pp. 287-291.

* cited by examiner

OPTOELECTRICAL VAPOR SENSING

CROSS-REFERENCE TO RELATED APPLICATIONS AND CLAIM OF PRIORITY

This application claims the benefit of U.S. Provisional Patent Application Ser. No. 61/316,487 filed on Mar. 23, 2010, which is hereby incorporated by reference in its entirety.

GOVERNMENT INTEREST

This invention was made with government support under Grants #CHE0641353 and #CBET0730667 awarded by the National Science Foundation. The Government has certain rights in this invention.

FIELD OF THE INVENTION

This invention relates generally to materials and chemical sensors. Therefore, the present invention relates generally to the fields of chemistry and materials science.

BACKGROUND

Various vapor sensing devices have been employed to provide a means for monitoring and controlling organic compounds. Such devices can include chemiresistors and semiconductors. Compared to the inorganic chemiresistors, organic semiconductors can offer facile deposition procedure as well as various choice and easy tuning of bind receptors for analyte molecules. Although organic field-effect transistors (FETs) can also be used as chemiresistors, the fabrication is relatively complicated and the performance is affected by many factors, like boundary grain, surface morphology, molecular structure, etc. As such, novel sensor devices continue to be sought through ongoing development and research efforts.

SUMMARY

It has been recognized that it would be advantageous to develop a chemical sensor compound for detecting various materials.

As such, the present disclosure provides a chemical sensor, comprising: a nanofiber mass of p-type nanofibers, said nanofibers having a HOMO level greater than −5.0 eV; oxygen in contact with the p-type nanofibers; and a pair of electrodes in electrical association across the nanofiber mass; where the p-type nanofibers conduct an electric current that decreases upon contact with a amine compound.

Additionally, a method of detecting trace amine compounds can comprise contacting the amine compound with a nanofiber mass of p-type nanofiber, said nanofibers having a HOMO level greater than −5.0 eV, and measuring a change in electric current associated with the nanofiber mass before and after contacting the nanofiber mass with the amine compound.

BRIEF DESCRIPTION OF THE DRAWINGS

Features and advantages of the invention will be apparent from the detailed description which follows, taken in conjunction with the accompanying drawings, which together illustrate, by way of example, features of the invention; and, wherein.

Figure 1A:
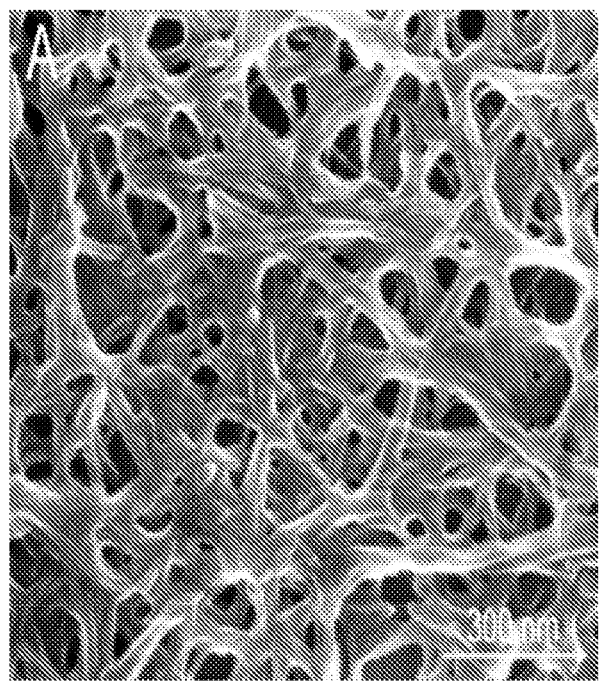
FIG. 1A is an SEM image of entangled alkyl-substituted, carbazole-cornered, arylene-ethynylene tetracyclic macromolecule (TDTC) nanofibers deposited on glass in accordance with one embodiment of the present invention.

These figures are not necessarily to scale and actual dimensions may, and likely will, deviate from those represented. Thus, the drawings should be considered illustrative of various aspects of the invention while not being limiting. Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENTS

Before the present invention is disclosed and described, it is to be understood that this disclosure is not limited to the particular process steps and materials disclosed herein because such process steps and materials may vary somewhat. It is also to be understood that the terminology used herein is used for the purpose of describing particular embodiments only. The terms are not intended to be limiting because the scope of the present disclosure is intended to be limited only by the appended claims and equivalents thereof.

It must be noted that, as used in this specification and the appended claims, the singular forms "a," "an," and "the" include plural referents unless the context clearly dictates otherwise.

As used herein, "alkyl" refers to a branched, unbranched, or cyclic saturated hydrocarbon group, which typically, although not necessarily, contains from 1 to about 50 carbon atoms, or 1 to about 40 carbon atoms, or 1 to about 30 carbon atoms for example. Alkyls include, but are not limited to, methyl, ethyl, n-propyl, isopropyl, n-butyl, isobutyl, t-butyl, octyl, and decyl, for example, as well as cycloalkyl groups such as cyclopentyl, and cyclohexyl, for example. As used herein, "substituted alkyl" refers to an alkyl substituted with one or more substituent groups. The term "heteroalkyl" refers to an alkyl in which at least one carbon atom is replaced with a heteroatom. If not otherwise indicated, the term "alkyl" includes unsubstituted alkyl, substituted alkyl, lower alkyl, and heteroalkyl.

As used herein, "nanofiber" refers to any elongated structure having a nanoscale cross-section such as, but not limited to, nanowires, nanobelts, nanoribbons, or other nanofibrous materials.

As used herein, "TDTC" refers to an alkyl-substituted, carbazole-cornered, arylene-ethynylene tetracyclic macromolecule having the structure of Formula 1:

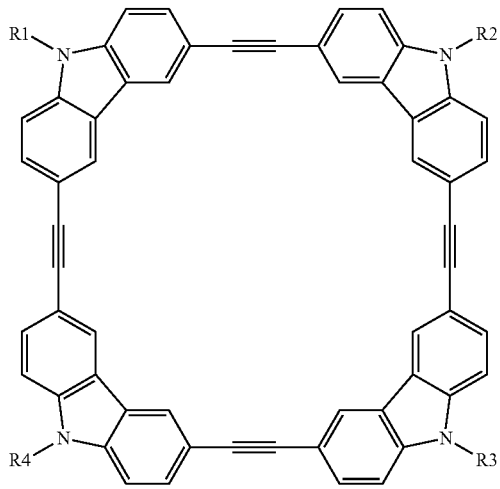

where R1-R4 are linear alkyl $C_{14}H_{29}$ chains.

As used herein, "ACTC" refers to a reference alkyl-substituted, carbazole-cornered, arylene-ethynylene tetracyclic macromolecule, having the structure of Formula 1:

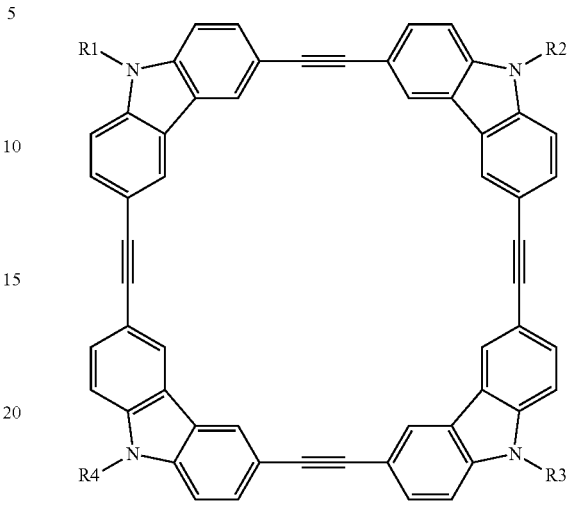

where R1-R4 is $(C=O)OC(CH_3)_2(CH_2)_{11}CH_3$.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 wt % to about 5 wt %" should be interpreted to include not only the explicitly recited values of about 1 wt % to about 5 wt %, but also include individual values and sub-ranges within the indicated range. Thus, included in this numerical range are individual values such as 2, 3.5, and 4 and sub-ranges such as from 1-3, from 2-4, and from 3-5, etc. This same principle applies to ranges reciting only one numerical value. Furthermore, such an interpretation should apply regardless of the breadth of the range or the characteristics being described.

The present inventors have discovered the effective photodoping of p-type organic nanofibers assembled from a suitable p-type molecule, and the application of the high photoconductivity thus obtained in vapor sensing of compounds. In one example, the compounds can be amines.

Specifically, in one embodiment, a chemical sensor can comprise a nanofiber mass of p-type nanofibers having a highest occupied molecular orbital (HOMO) level greater than −5.0 eV. Additionally, the chemical sensor can comprise oxygen in contact with the p-type nanofibers. In one aspect, the oxygen can be free oxygen. Further, the chemical sensor can comprise a pair of electrodes in electrical contact across the nanofiber mass, where the p-type nanofibers conduct an electric current that decreases upon contact with an amine compound.

The sensory materials described herein can be of p-type semiconductor, where the major charge carriers are holes, which can feasibly be depleted by surface adsorbed reductive species like amines resulting in decease in the electrical conductivity. Without being bound by any particular theory, the photoresponse is apparently a result that the reductive compounds can capture holes and in turn decrease the photocurrent. The electron doping can be initiated by a photo-induced electron transfer (charge separation) from the p-type organic molecule to oxygen. The ground-state charge-transfer complex formed between p-type organic molecule and oxygen appears to be responsible for the subsequent high photocurrent. Combination of the sensitive conductivity modulation with the unique features intrinsic to the nanofibril film (large surface area, continuous nanoporosity) can enable efficient vapor sensing of amines.

As such, the present nanofibers can be formed of any suitable p-type material which has a sufficiently low ionization energy (e.g. sufficiently high HOMO level) to form a ground state charge-transfer complex with the surface adsorbed oxygen. Thus, photoconductivity of the material can be obtained through simply photodoping of the p-type organic nanofibers with oxygen. As discussed herein, photo-illumination of the charge-transfer complex leads to charge separation, leaving positive charges (holes) within the nanofiber acting as the charge carriers. An increase in charge carrier density in turn results in high photocurrent upon light irradiation. Thus, suitable p-type organic fiber materials can be photodoped to produce a chemiresistor sensor based on photocurrent, rather than intrinsic electrical current of the channel materials.

The ground state complex formation between oxygen and the organic molecule is dependent on the relative redox potentials of the two species, which act as electron acceptor and donor, respectively. In general, the lower the ionization potential (or high HOMO level) of the organic molecule, the stronger the complexation will be. For example, alkyl-substituted, carbazole-cornered, arylene-ethynylene tetracyclic macromolecule (TDTC) possesses high HOMO and is capable of forming a D-A complex with oxygen, which in turn enables efficient charge separation upon photo-illumination. In contrast, the HOMO of ACTC is about 0.7 eV lower than that of TDTC, thus diminishing the capability of forming complex with oxygen, as discussed in detail herein; i.e., there was no photocurrent observed for the ACTC nanofibers under the same ambient conditions.

Generally, the building block molecules of the nanofibers of the present disclosure, that fulfill the efficient photodoping and electrical vapor sensing, can satisfy the following guidelines: 1) a molecular structure that allows for 1D self-assembly into nanowires, nanofibers, or nanobelts; 2) sufficiently low ionization energy for forming a complex with oxygen thus enabling photoinduced charge separation to produce free charge carriers; and 3) effective intermolecular stacking or electronic interaction so that the generated charges within the nanofibers can transport effectively towards the electrodes, leading to overall high photoconductivity. In one aspect, the nanofibers can be formed of an electrically neutral compound (i.e. neutral at ambient conditions).

One example of a molecule that can be used to form the nanofibers include alkyl-substituted, carbazole-cornered, arylene-ethynylene tetracyclic macromolecules of formula 1:

Formula 1

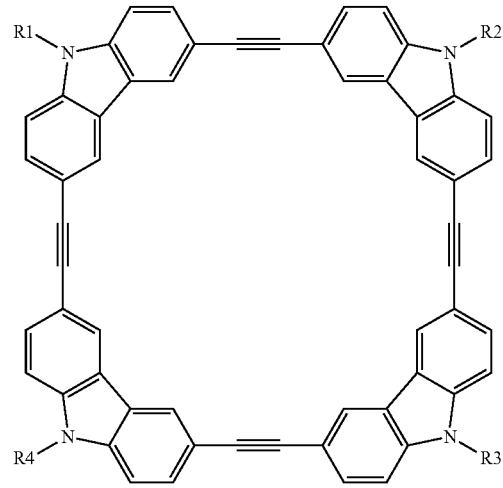

where R1-R4 are alkyl groups and wherein at least some of the macromolecules are cofacially stacked (e.g. cofacially stacked along nanofibers). In one embodiment, R1-R4 can be individually selected from $C_3$ to $C_{18}$ alkyl chains. The alkyl chains can be straight chains, branched, and/or substituted. In one aspect, R1-R4 can be $C_{14}$ alkyl chains. In one specific aspect, R1-R4 can be $C_{14}$ linear alkyl chains.

Other suitable molecules useful for forming the nanofibers can include an indolocarbazole derivative. Non-limiting examples of suitable indolocarbazole derivatives include

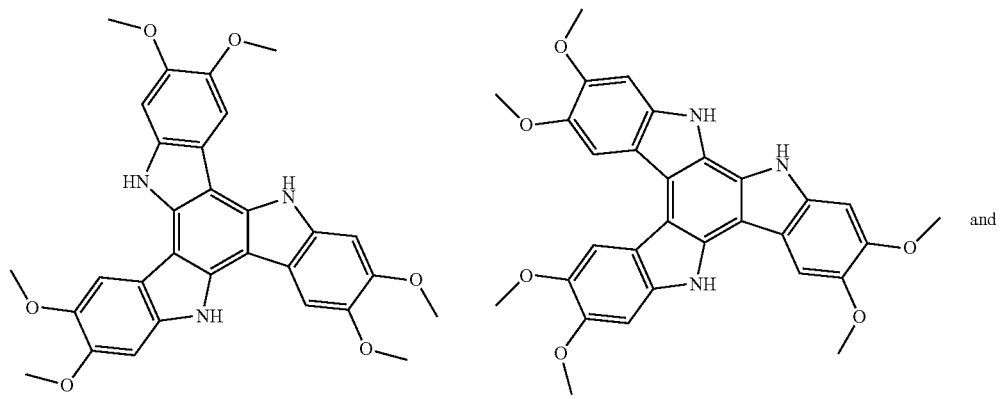

and

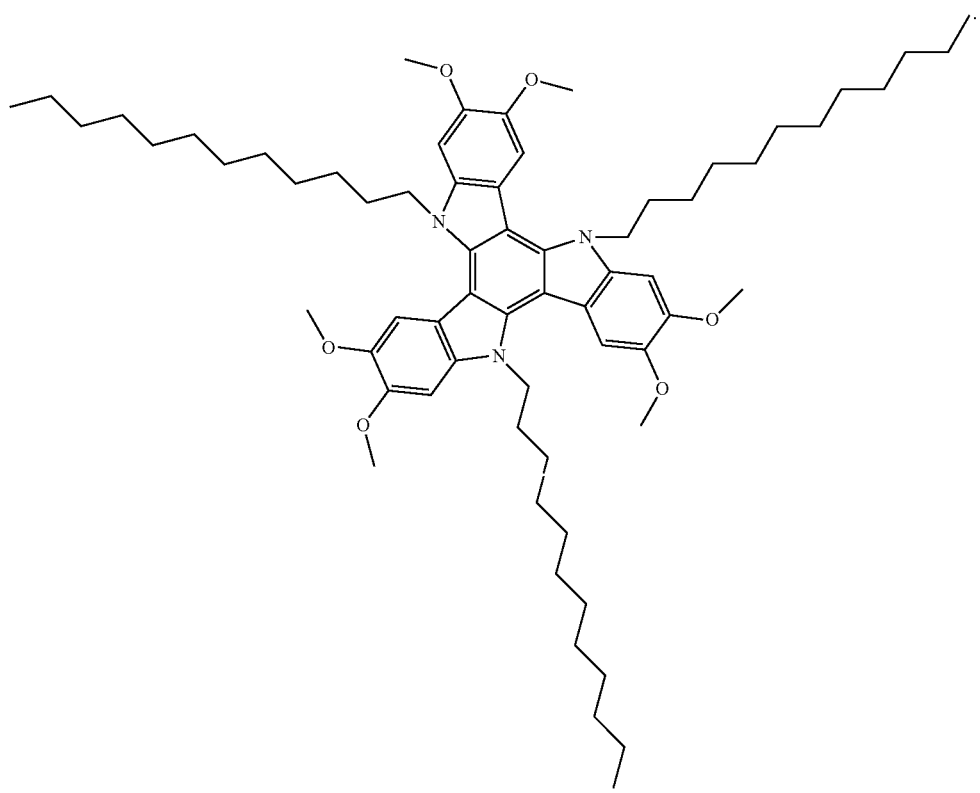

In one aspect, the ionization energy of the nanofiber is greater than −4.9 eV.

In one embodiment, the reductive compound can be an amine. In one specific aspect, the amine can be aniline or alkyl amines. Additionally, the amine compound can be adsorbed for an extended period of time so as to increase reliability of readings. Accordingly, in one aspect, the electrical current can be decreased for at least 5 minutes after exposure to the amine compound. In another aspect, the electrical current can be decreased for at least 10 minutes after exposure to the amine compound. In one embodiment, the amine compound can adsorb on the nanofiber mass for at least 5 minutes. In one aspect, the amine compound can adsorb on the nanofiber mass for at least 10 minutes.

The nanofiber mass can be deposited on the electrode. Additionally, the nanofiber mass can be a film. In one embodiment, the chemical sensor can detect the amine compound in a concentration of at least 1 ppm. In one aspect, the chemical sensor can detect the amine compound in a concentration of at least 1 ppb. In another aspect, the chemical sensor can detect the amine compound in a concentration of at least 1 ppt.

The chemical sensor can be selective of the amine compound over other organic compounds. In one embodiment, the chemical sensor can be selective by measuring a different electric current affected by the amine compound compared to the other organic compounds or by measuring a different length of time that the electric current is affected by the amine compound as compared to the other organic compounds.

A method of detecting trace amine compounds can comprise contacting the amine compound with a nanofiber mass of p-type nanofiber comprising a molecule such as those previously listed. Additionally, the method can comprise measuring a change in electric current associated with the nanofiber mass before and after contacting the nanofiber mass with the amine compound.

In one embodiment, the change in electric current can decrease by at least 1% after the nanofiber mass is contacted with the amine compound. In one aspect, the change in electric current can decrease by at least 3% after the nanofiber mass is contacted with the amine compound. In another aspect, the change in electric current can decrease by at least 5% after the nanofiber mass is contacted with the amine compound.

In one embodiment, the change in electric current can be measurable when the nanofiber mass contacts the amine compound in a concentration of at least 1 ppm. In one aspect, the change in electric current can be measurable when the nanofiber mass contacts the amine compound in a concentration of at least 1 ppb. In another aspect, the change in electric current can be measurable when the nanofiber mass contacts the amine compound in a concentration of at least 1 ppt.

Additionally, the method can further comprise differentiating between the amine compound and other organic compounds. In one embodiment, the differentiating can be by measuring a different electric current affected by the amine compound compared to the other organic compounds or by measuring a different length of time that the electric current is affected by the amine compound as compared to the other organic compounds.

The nanofiber mass can be formed in any suitable manner. However, in one aspect, the mass can be formed by injecting chloroform solution of TDTC into ethanol in a test tube with stirring and then aging for 2 days in a refrigerator.

The methods and sensors described herein can be used in the area selected from the group consisting of air pollution monitoring and controlling, food quality control, medical diagnosis, and security. Moreover, the fabricated photoconductive nanofibers provide unique and advantageous features in comparison to the bulk-phase materials (e.g., films). These features include more organized crystalline structure, 1D confinement and enhancement of optoelectronic properties favorable for long-range exciton and charge migration, and a large surface area conducive to surface modification. Moreover, when deposited onto a substrate the large number of entangled nanofibers form highly porous film, with continuous, size variable open pores that facilitate the gas collection and diffusion throughout the whole materials. Combination of these features makes the 1D nanomaterials ideal vapor detection via optical (emission quenching) or an electrical sensing mode. Additionally, the sensors can be aimed for detecting a class of vapor species (molecules), rather than for identifying a single specific compound.

Figure 1B:
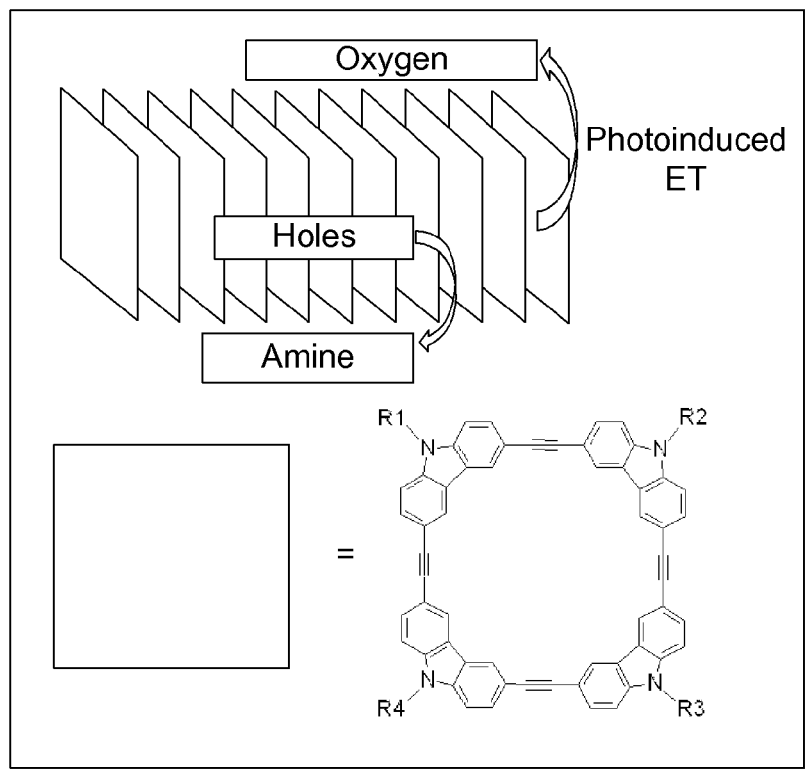
FIG. 1B is an enhanced schematic illustration showing the enhancement of conductivity through photodoping (i.e., photoinduced electron transfer from TDTC to oxygen, leaving holes within the nanofiber) and the decrease in conductivity in accordance with one embodiment of the present invention.
Figure 2:
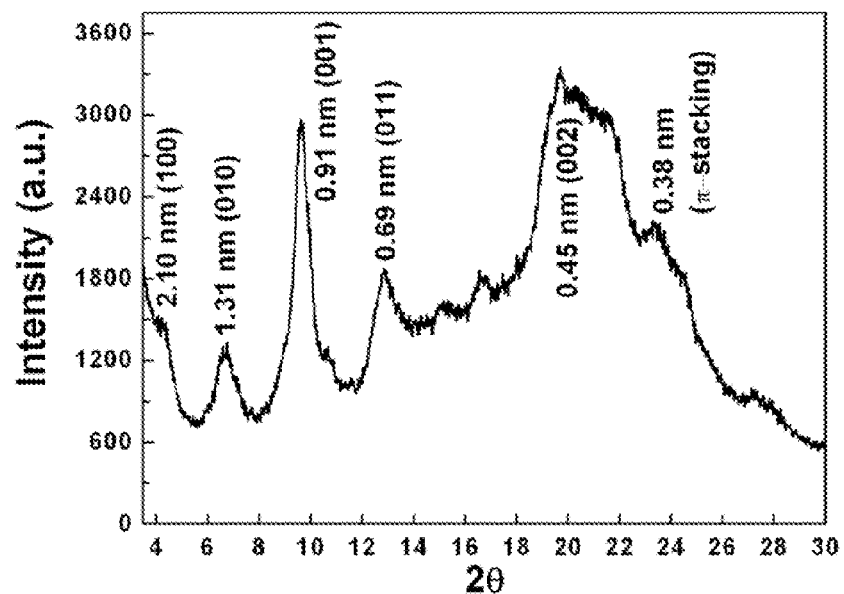
FIG. 2 is an XRD spectrum of the TDTC nanofibers in accordance with one embodiment of the present invention.
Figure 3:
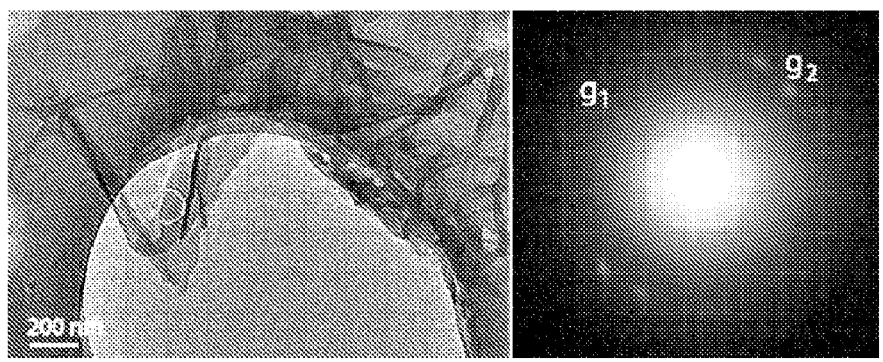
FIG. 3 is a TEM image (left) and E-diffraction pattern (right) recorded over the TDTC nanofibers cast on a carbon film with two reciprocal diffraction vectors ($g_1$, $g_2$) marked, giving two d-spacings, d1=0.94 nm and d2=1.24 nm in accordance with one embodiment of the present invention.
Figure 4:
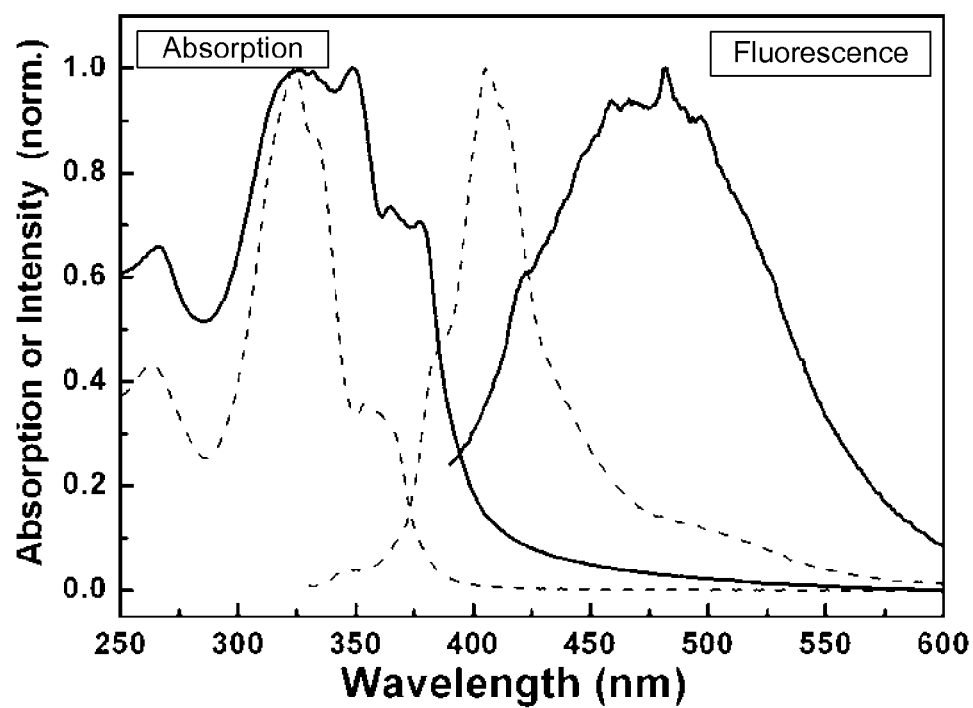
FIG. 4 is a plot of absorption (left) and fluorescence (right) spectra of TDTC in chloroform solution (dashed) and the nanofiber state (solid) in accordance with one embodiment of the present invention.

Turning now to the Figures, FIG. 1 shows the SEM image of the nanofibers fabricated from alkyl-substituted, carbazole-cornered, arylene-ethynylene tetracyclic macromolecules of Formula 1 where R1-R4 is linear alkyl chains of $C_{14}H_{29}$ (TDTC), through a simple solution-based self-assembly. The obtained nanofibers are about 20-50 nm in diameter and several micrometers in length. The extended 1D molecular arrangement is thought to be dominated by the $\pi$-$\pi$ interaction between the planar TDTC molecules (FIG. 1). Such cofacial $\pi$-$\pi$ stacking is clearly indicated by the d-spacing (3.8 Å) as observed in the XRD spectrum (FIG. 2), which corresponds to a regular $\pi$-$\pi$ stacking distance. Electron diffraction from the nanofiber showed a crystal like pattern with sharp diffraction spots (FIG. 3), producing two distinct, reciprocal lattice vectors, giving two d-spacings, d1=0.94 nm and d2=1.24 nm, which are consistent with the XRD spectrum (FIG. 2). Such strong $\pi$-$\pi$ interaction is also consistent with the new absorption band emerged at longer wavelength (centered 377 nm) as measured for the nanofibers in comparison to the molecular solution of TDTC (FIG. 4).

The elegance of the present systems lie in the simplicity of the photodoping process, for which the photoinduced electron transfer is initiated between TDTC and the surface adsorbed oxygen under ambient conditions, leaving positive charges (holes) within the nanofiber acting as the major charge carriers.

Figure 5A:
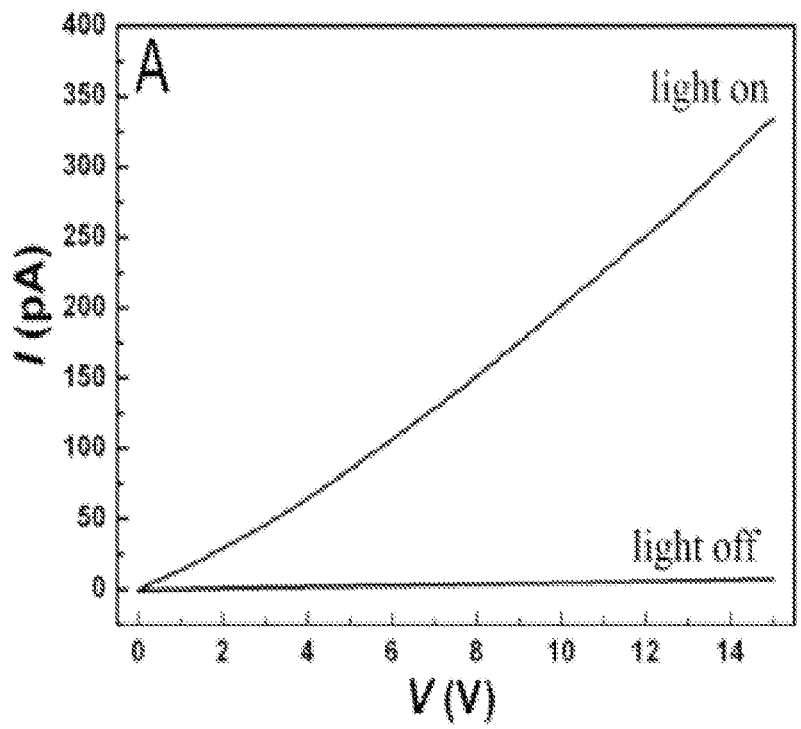
FIG. 5A is a plot of I-V curves measured over TDTC nanofibers in the dark (upper) and under the white light irradiation at power density of 0.3 mW/mm$^2$ (lower) in accordance with one embodiment of the present invention.
Figure 5B:
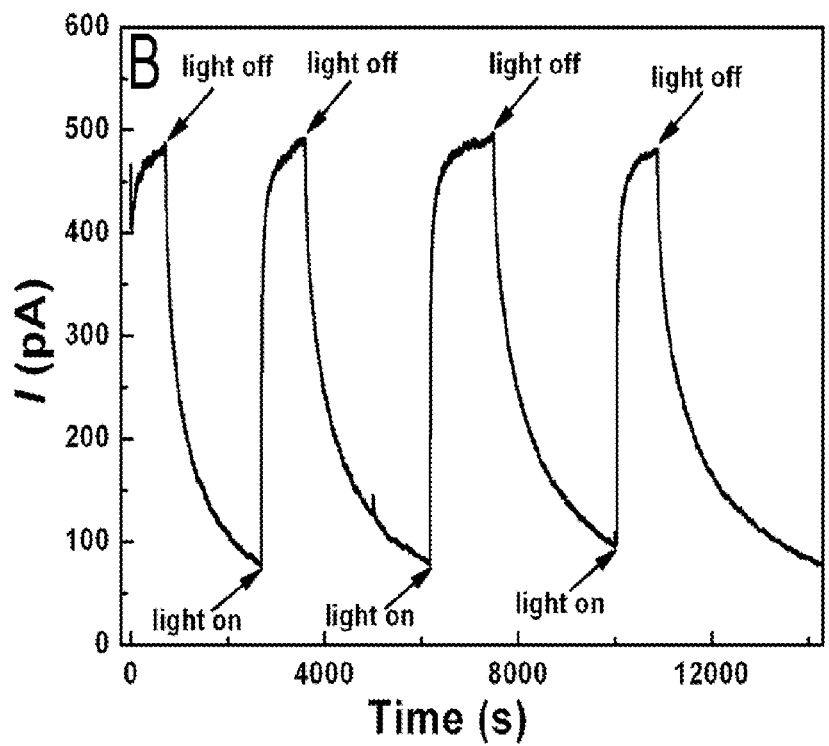
FIG. 5B is a plot of photocurrent (at 10V) in response to turning on and off the irradiation in accordance with one embodiment of the present invention.
Figure 5C:
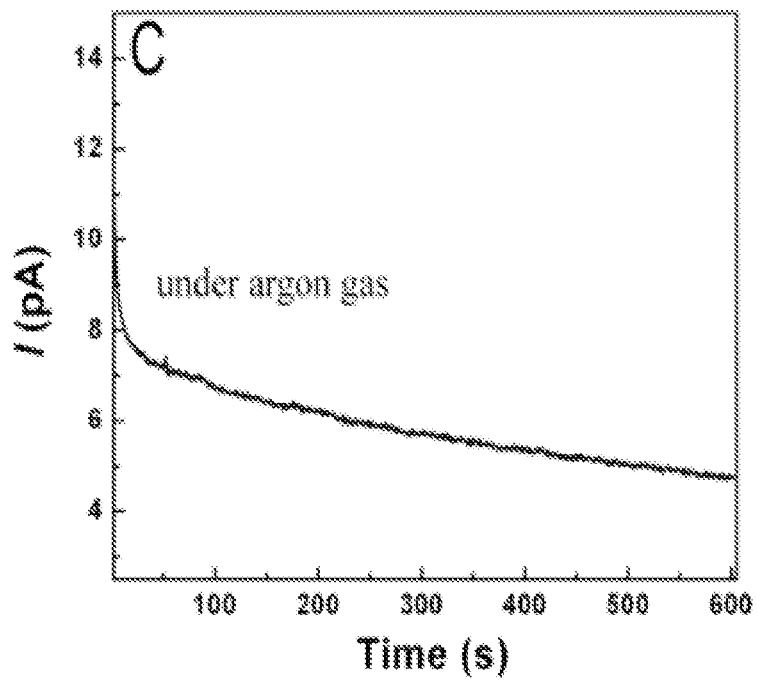
FIG. 5C is a plot of photocurrent change (at 10V) with time following argon gas introduction (monitored 25 min after argon gas started) in accordance with one embodiment of the present invention.
Figure 6A:
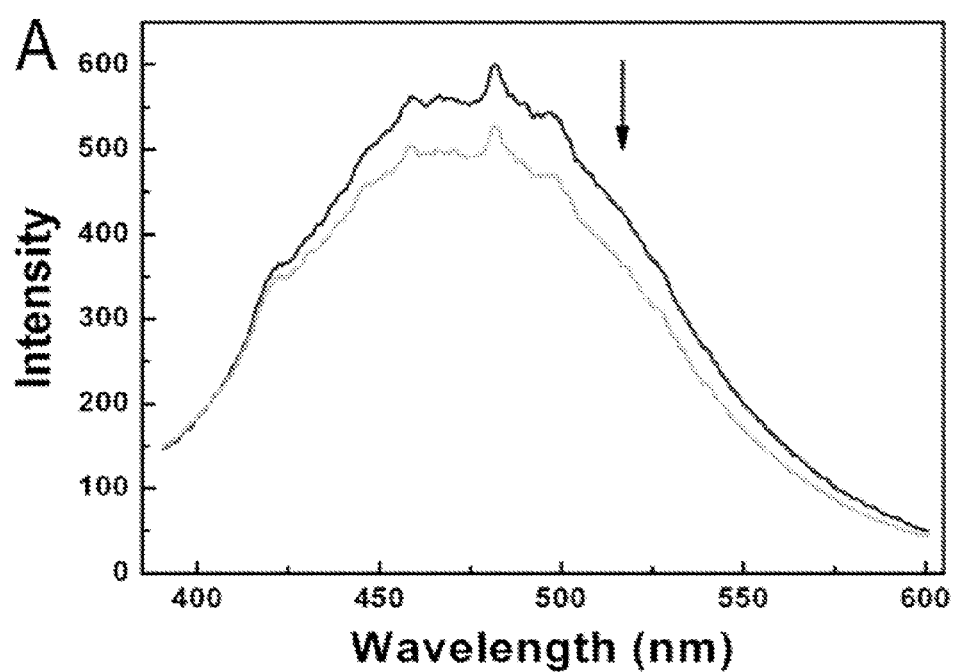
FIG. 6A is a plot of fluorescence emission spectra of TDTC nanofibers under argon gas (upper) and ambient condition (lower) in accordance with one embodiment of the present invention.

The nanofibers obtained exhibited high conductivity upon irradiation with white light under ambient condition, whereas negligible current was observed in the dark (FIG. 5A). The photoconduction switching has also proven to be reversible with the light turning on and off (FIG. 5B), implying the high stability of the materials when operated under ambient condition. The high photoconductivity observed is likely correlated to the presence of oxygen, which can usually help increase the concentration of holes for p-type organic materials. To confirm the effect of oxygen, the same photocurrent measurements was performed under argon protection (FIG. 5C). Upon introducing an argon atmosphere, the photocurrent gradually decreased, and eventually reached the value measured in the dark. This observation clearly implied that the photoconductivity originated from the photoinduced charge separation between TDTC and oxygen, which is supported by the low ionization potential (i.e. high HOMO level) of TDTC. The proposed photoinduced charge separation is consistent with the fluorescence quenching by oxygen observed for the nanofibers, for which the emission intensity decreased about 13% in air compared to that measured under argon (FIG. 6A). Without intending to be bound by any particular theory, two possible mechanisms for the photoinduced charge separation are: intermolecular electron transfer from the photoexcited state of TDTC to surface adsorbed oxygen, and an intramolecular charge transfer process within the ground donor-acceptor complex formed between TDTC and oxygen as previously observed for the reducing conjugated polymers.

To further clarify the role played by oxygen in the photocurrent generation, a reference tetracyclic macromolecule, named ACTC having the structure of Formula 1 where R1-R4 is $(C=O)OC(CH_3)_2(CH_2)_{11}CH_3$, was chosen as the building-block to perform the same investigations for comparison with TDTC.

Figure 6B:
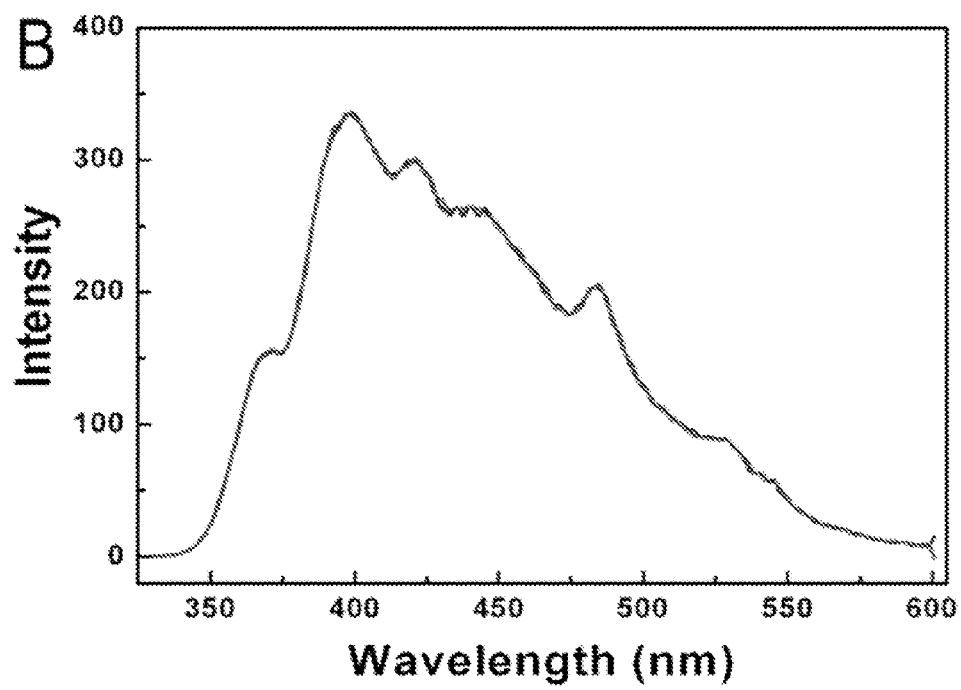
FIG. 6B is a plot of fluorescence emission spectra of ACTC nanofibers under argon gas (solid) and ambient condition (dotted) in accordance with one embodiment of the present invention.
Figure 7:
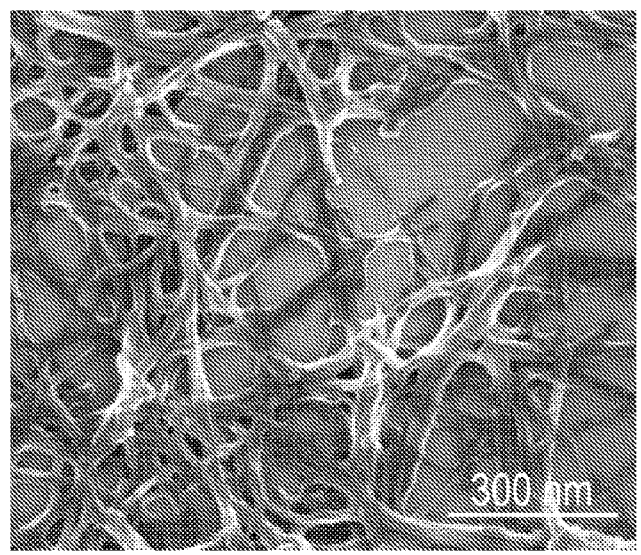
FIG. 7 is an SEM image of the nanofibers fabricated from ACTC in accordance with one embodiment of the present invention.
Figure 8A:
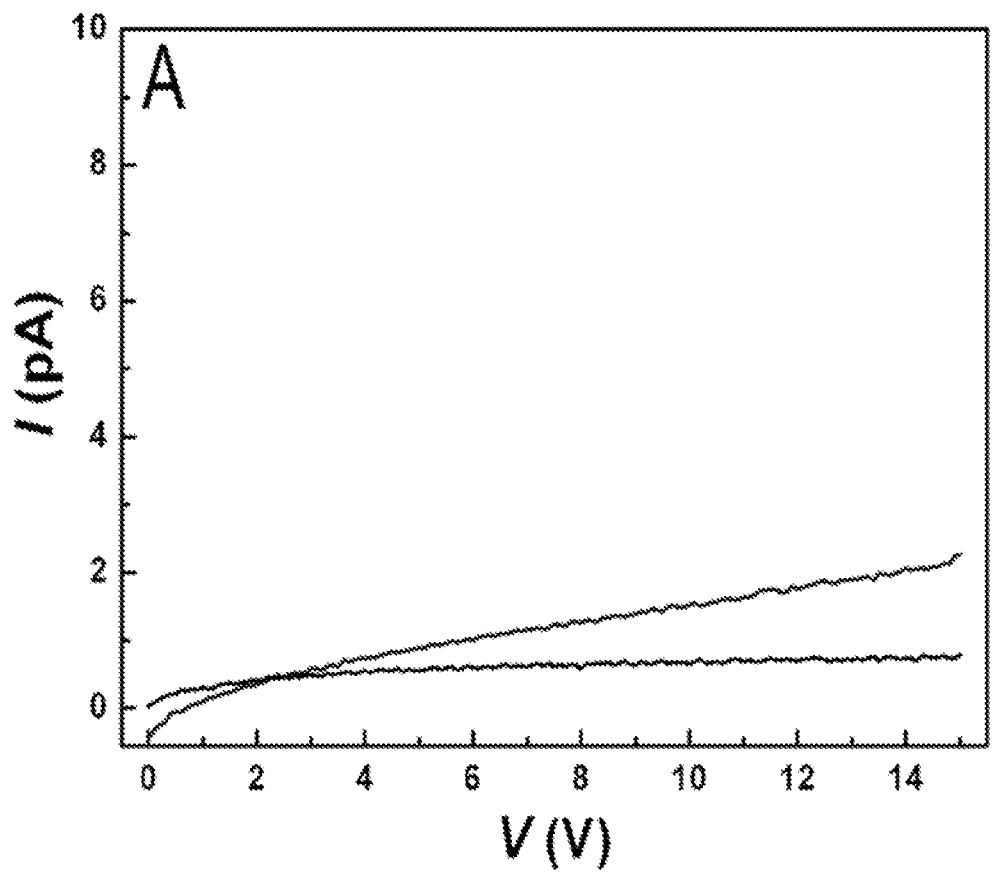
FIG. 8A is a plot of I-V curves measured over ACTC nanofibers in the dark (lower) and under the irradiation of white light at power density of 0.3 mW/mm$^2$ (upper) in accordance with one embodiment of the present invention.
Figure 8B:
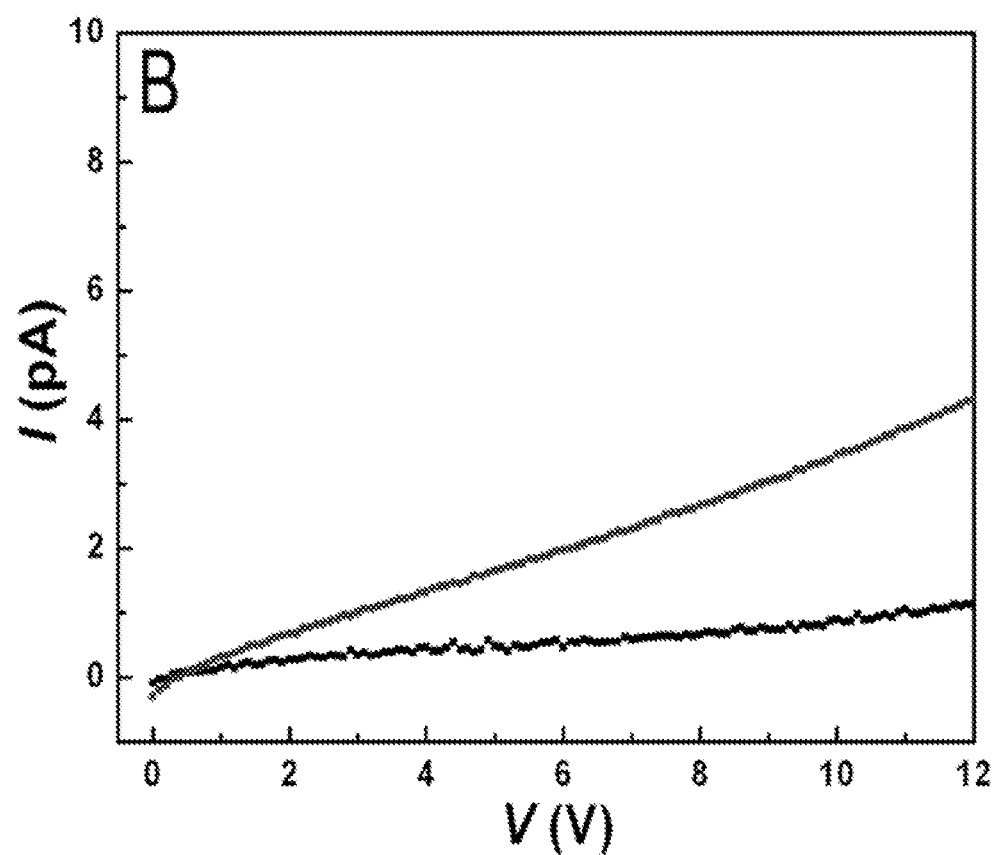
FIG. 8B is a plot of I-V curves measured over ACTC nanofibers in the dark (lower) and under the irradiation of UV light (from a mercury lamp) at power density of 2 mW/mm$^2$ (upper) in accordance with one embodiment of the present invention.

ACTC possesses the same $\pi$-skeleton but substituted with an acyl-linked alkyl side-chains, which produces almost the same lowest unoccupied molecular orbital (LUMO) as that of TDTC, while decreases the HOMO level by as much as 0.7 eV compared to that of TDTC. Although similar nanofibers were fabricated from ACTC using the same method (FIG. 7), negligible photocurrent was generated for these nanofibers under the same irradiation conditions as performed for the TDTC fibers (FIG. 8). Even under irradiation with UV light (to get direct excitation of the building-blocks), there was still no obvious photocurrent enhancement observed, excluding the possibility of electron transfer from the photoexcited state (i.e., LUMO) of ACTC to oxygen. This is consistent with fluorescence measurements performed on the same nanofibers, for which the presence of oxygen exhibited no influence on the emission intensity of the nanofibers (FIG. 6B). Together, these observations suggest that the photocurrent generation in the TDTC nanofibers is due to photoinduced intramolecular charge separation of surface complexes between the TDTC and adsorbed oxygen. The lack of formation of such ground state complex with ACTC is likely due to its high ionization potential.

Figure 5D:
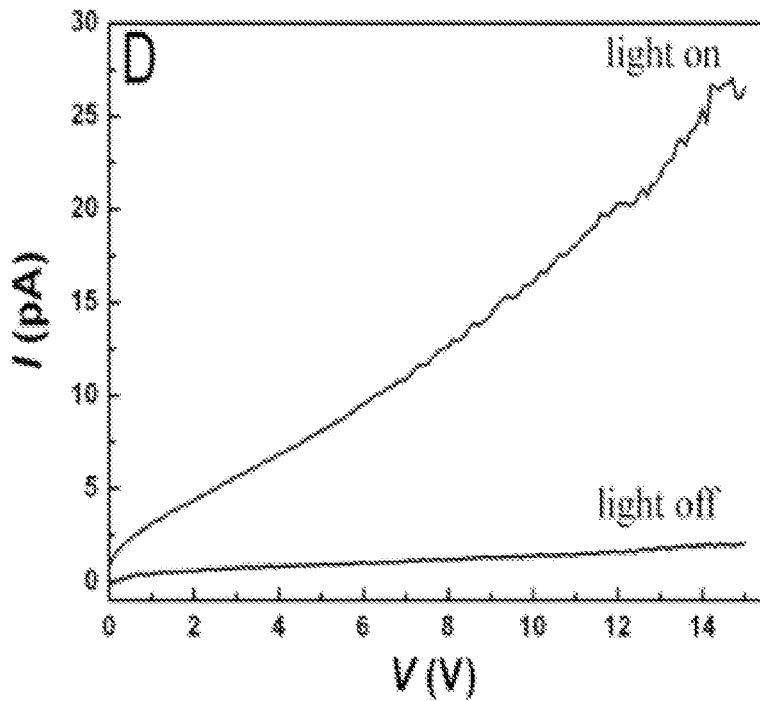
FIG. 5D is a plot of I-V curves measured over a spin-cast film of TDTC in the dark (lower) and under the same white light irradiation as used in A) (upper) in accordance with one embodiment of the present invention.

While not intending to be bound by any particular theory, the present inventors has theorized that the cofacial stacking of the TDTC molecules along the long axis of nanofiber enables long range delocalization of the photogenerated charges similar to other 1D assemblies, thus leading to further enhancement of the conductivity. This is in contrast to the photodoping of film based materials, where the poor intermolecular organization often limits the charge transport. In support of these theory, the same photocurrent measurement was performed over the spin-cast film of TDTC (FIG. 5D), for which only slight enhancement of photocurrent was obtained.

Figure 9A:
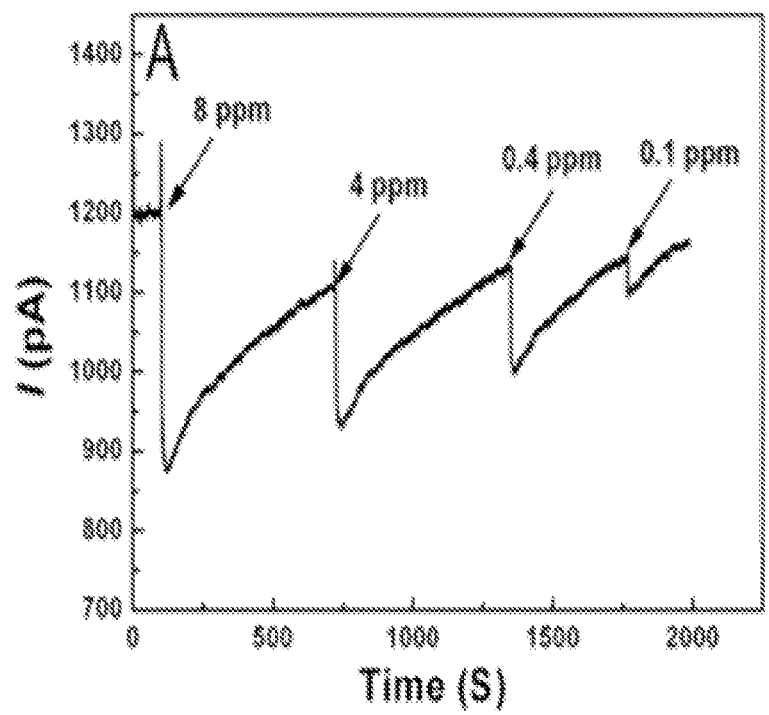
FIG. 9A is a plot of photocurrent change of TDTC nanofibers upon exposure to aniline vapor at various pressures in accordance with one embodiment of the present invention.

Taking advantage of the large surface area and 3D porosity intrinsic to the nanofibers when deposited onto a substrate in a film format, the nanofibers fabricated from TDTC are expected to function as chemiresistor for trace vapor sensing of reducing reagents (e.g., amines) through modulation of the electrical current. Aniline was chosen as the target analyte here due to its relatively low saturated vapor pressure (allowing for easy dilution down to ppb range) and its popular use as precursor in chemical industry. As shown in FIG. 9A, the photoconductivity of the nanofibers is very sensitive to aniline vapor. Upon exposure to 0.1 ppm of aniline, significant decrease in photocurrent (3%) was observed. Considering the fact that a well-shielded electrical measuring unit can detect a current change as small as below 0.1%, the nanofibril system shown in FIG. 9 can already detect aniline down to ppb and even sub ppb levels. Moreover, the photocurrent response to aniline vapor is reversible, facilitating the practical application of the sensing system.

Figure 9B:
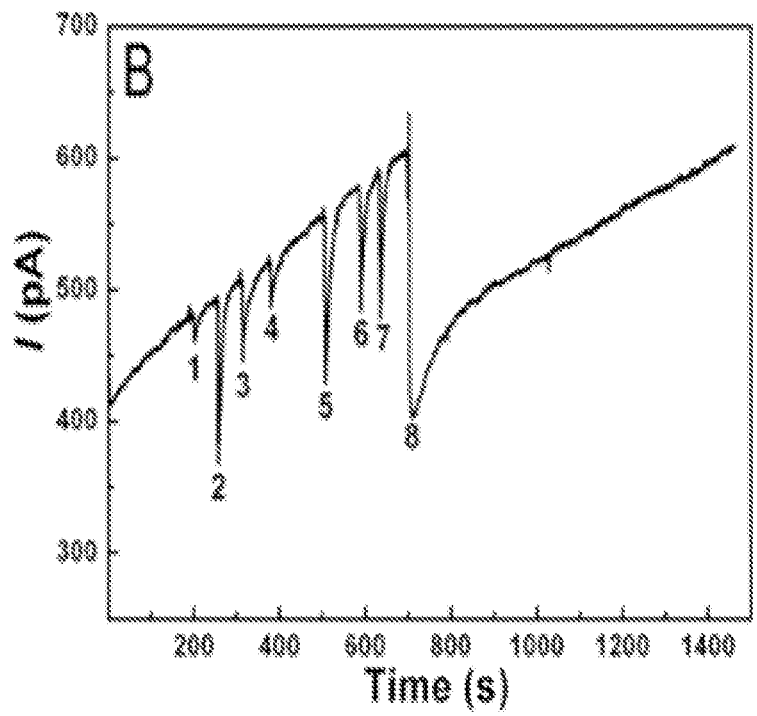
FIG. 9B is a plot of photocurrent change measured over the same nanofibers in FIG. 9A upon exposure to common organic vapors at high vapor pressures: (1) Chloroform, 3500 ppm; (2) acetone, 4100 ppm (3); hexane:2600 ppm (4) toluene, 750 ppm; (5) THF, 3500 ppm; (6) ethanol, 1500 ppm; (7) nitromethane, 1400 ppm; (8) aniline, 25 ppm in accordance with one embodiment of the present invention.
Figure 10:
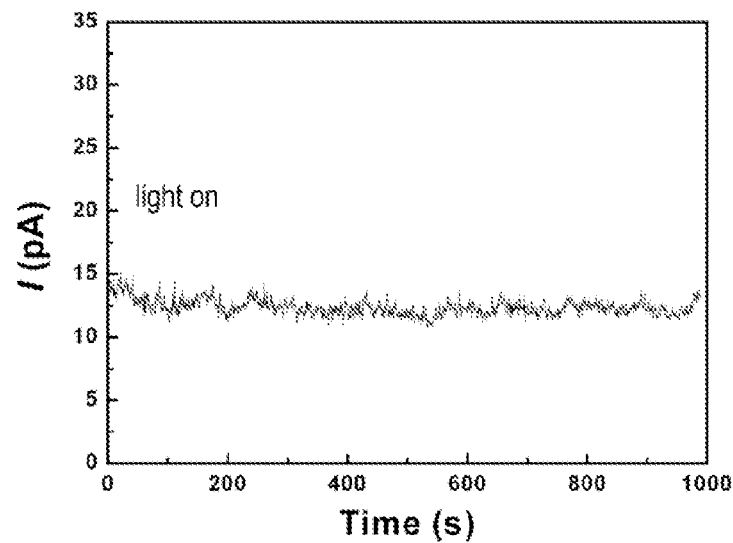
FIG. 10 is a graph of photocurrent change (at 10V) of TDTC film with time following argon gas introduction (monitored 25 min after argon gas started) in accordance with one embodiment of the present invention.
Figure 11:
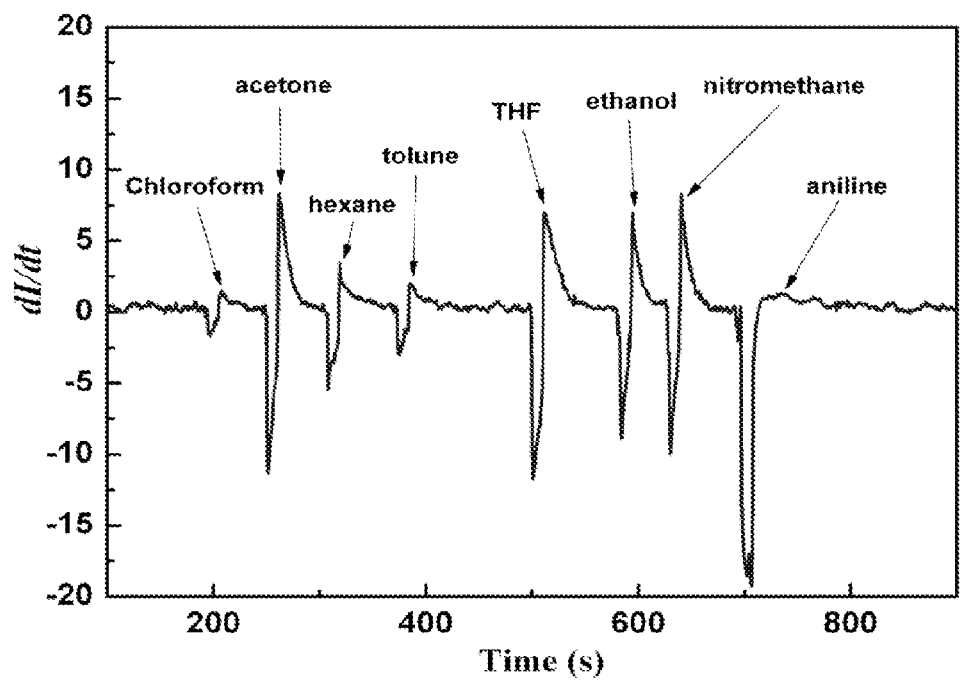
FIG. 11 is a graph of first order differentiation of FIG. 9B (dI/dt vs. time) showing the different response to aniline as compared to the 7 reference reagents vapor in accordance with one embodiment of the present invention.

The vapor sensing with the nanofibers was also tested against the common organic reagents, as shown in FIG. 9B, aiming to verify the sensing selectivity towards amines. Despite the much higher vapor pressure, the photoresponse observed for the organic vapors was much smaller than that observed for aniline. Moreover, the photocurrent change upon exposure to common organic vapors can be recovered completely within 30 seconds. Such rapid fluctuation in current is likely due to the surface desorption of oxygen caused by blowing of the organic vapor. Due to the weak physical adsorption of these organic species on the nanofiber, they can be quickly replaced by oxygen upon re-equilibration with air, thus recovering the photoconductivity. In comparison, the recovery of photocurrent after exposure to aniline vapor was in the time range of 10 min or longer, which is apparently attributed to the strong binding between amine and the positively charged nanofiber (under irradiation). The much delayed recovery of current thus observed for the aniline may be used as a signature (via digital differentiation, FIG. 11) for selective detection of amines against the common organic vapors.

To this end, the sensing systems of the present invention can provide good selectivity for detecting amines against other common liquids or solvents, including those listed in FIG. 9B. Such selectivity relies on the different recovery rate after exposure to amines in comparison to other reagents. As shown in FIG. 9B, the photocurrent change upon exposure to common organic vapors can be recovered completely within 30 seconds, whereas the recovery in the case of aniline vapor takes more than 10 min. The much slower recovery of current thus observed for the aniline can be used as a signature (via digital differentiation) for selective detection of amines against the common organic vapors. Indeed, the first order differentiation (dI/dt vs. time) of FIG. 9B (as shown in the FIG. 11) demonstrate clearly the different signal shape for aniline as compared to the reference reagents vapor. While a nearly symmetric "pulse" signal was observed for the later, the response to aniline remained asymmetric with negligible signal on the positive side. Furthermore, considering the fact that the vapor pressures of the reference reagents employed are about 2 orders of magnitude higher than that of aniline, the sensing selectivity for aniline as depicted in FIG. 9B is prominent. All the sensing tests were performed under ambient conditions, and there was no significant effect of humidity on the electrical conductivity of these materials.

As such, the present sensors can provide well-defined p-type organic nanofibers. High photoconductivity can be achieved for these nanofibers though a simple photodoping process under ambient condition. The high photoconductivity obtained for the nanofibers, combining with their intrinsic high surface area and porosity, can enable efficient electrical vapor sensing of organic amines.

Further, as discussed herein, the present sensors can find broad applications in health and security examination including:

1. Air quality and security: mainly for in-field monitoring of air quality against pollution by toxic amines, which have commonly been used in various industry and military systems. Particularly, hydrazine has been heavily used in both industry (as an oxygen scavenger and corrosion inhibitor) and military (as a fuel in rocket propulsion systems); moreover, this compound has been implicated as a carcinogen and is readily absorbed through the skin. Another typical toxic amine is ethanolamine, which has been used as the scrubbing agent in the ventilation system of submarines to remove carbon dioxide from the air. Due to their toxicity and reactivity, facile detection of these amines is relevant to both life and environment security.
2. Health and clinic: for rapid screening of uremia and lung cancer, one of the most popular cancers, particularly in the developing countries. Alkyl-amines can be used as the biomarkers for uremia diseases, while aromatic-amines can be used for lung cancer. Very trace amount of amines breathed out of the patient will be detected (at concentration of ppt), thus enabling rapid diagnostics or warning of the diseases at the early stage. The sensors will be designed in a way for easy, handful use by ordinary people.
3. Food industry: for high throughput quality control and monitoring by detecting the amines released from foods.

EXAMPLES

Example 1

Synthesis and Fabrication of Nanofibers

TDTC and ACTC were synthesized by following the previous method (described in detail in Naddo et al., Detection of Explosives with a Fluorescent Nanofibril Film, J. Am. Chem. Soc., 2007, 129, 6978-6979, which is incorporated herein by reference). All nanofibers were fabricated by injecting 0.4 mL chloroform solution of TDTC or ACTC (0.15 mM) into 3 mL ethanol in a test tube with stirring and then aging for 2 days in a refrigerator. The nanofibers thus formed can be transferred and cast onto glass surface by pipetting.

Example 2

Structural and Property Characterizations

UV-vis absorption and fluorescence spectra were measured on a PerkinElmer Lambda 25 spectrophotometer and LS 55 fluorometer, respectively. SEM measurement was performed with a FEI NanoNova 6300 microscope, and the samples were directly drop-cast on a silica substrate. The FEI NanoNova is a high resolution SEM allowing for direct imaging of non-conducting materials with feature size down to 2 nm. The X-ray diffraction was carried out with a Philips X'Pert XRD instrument. TEM measurement was performed on a JEOL 2010 instrument (LaB6, operated at 200 kV). Electron diffraction patterns were recorded using a CCD camera under controlled electron dose with low illumination intensity to reduce radiation damage of the sample. All the measurements were performed at room temperature using a 300 nm diameter probe.

Example 3

Photocurrent and Vapor Sensing Measurements

Electrical current measurements of the nanofibers were performed with an Agilent 4156C Precision Semiconductor Parameter Analyzer coupled with a Signatone S-1160 Probe Station housed in a metallic shielding box under ambient condition. The micro-gap electrodes were fabricated by photolithography on a silicon wafer covered with a 300-nm thick $SiO_2$ dielectric layer. The gold electrode pair is 14 μm long and 4 μm wide, on to which appropriate amount of nanofibers were deposited by drop-casting, followed by air-drying in the dark. A tungsten lamp (Quartzline, 21V, 150 W) and Mercury lamp (Newport, 200 W) was used as the white light source and UV light source, respectively. The light is guided into the probe station through a glass or quartz optical fiber, followed by focusing on the sample through the objective lens. The vapor sensing measurements were carried out by directly blowing diluted aniline or other common organic vapor onto nanofibers by a syringe.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A chemical sensor, comprising:
    a) a nanofiber mass of p-type nanofibers, said nanofibers having a HOMO level greater than −5.0 eV;
    b) oxygen in contact with the p-type nanofibers; and
    c) a pair of electrodes in electrical association across the nanofiber mass;
    wherein the p-type nanofibers conduct an electric current that decreases upon contact with a amine compound.

2. The chemical sensor of claim 1, wherein the nanofibers comprise a plurality of alkyl-substituted, carbazole-cornered, arylene-ethynylene tetracyclic macromolecules of formula 1:

Formula 1

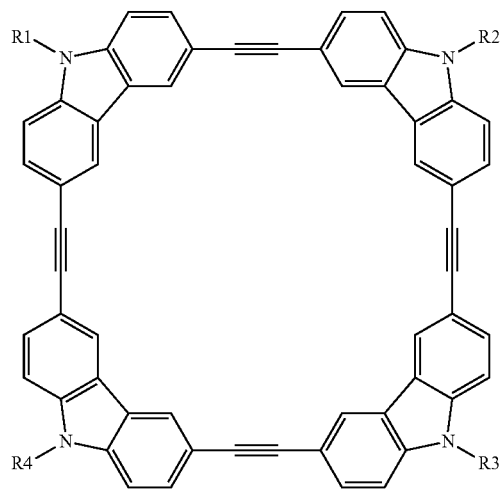

wherein R1-R4 are alkyl groups and wherein at least some of the macromolecules are cofacially stacked.

3. The chemical sensor of claim 2, wherein R1-R4 are individually selected from $C_3$ to $C_{18}$ alkyl chains.

4. The chemical sensor of claim 2, wherein R1-R4 are $C_{14}$ alkyl chains.

5. The chemical sensor of claim 1, wherein the nanofibers comprise an indolocarbazole derivative.

6. The chemical sensor of claim 5, wherein the indolocarbazole derivative is selected from the group consisting of

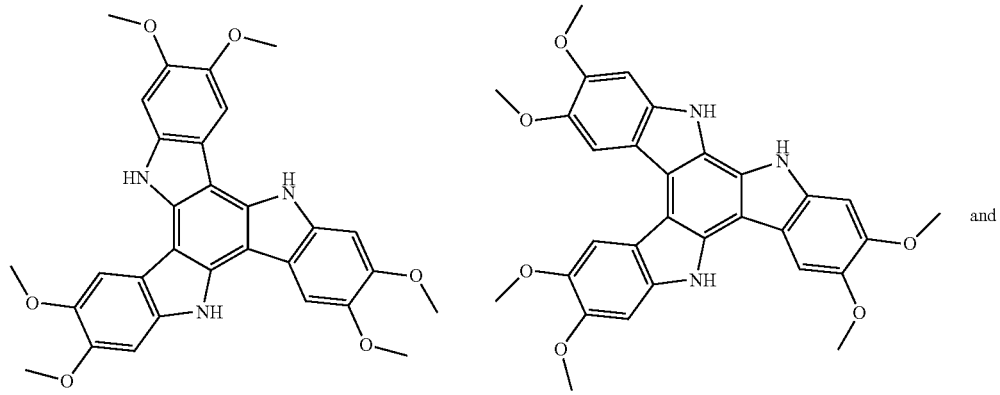

-continued

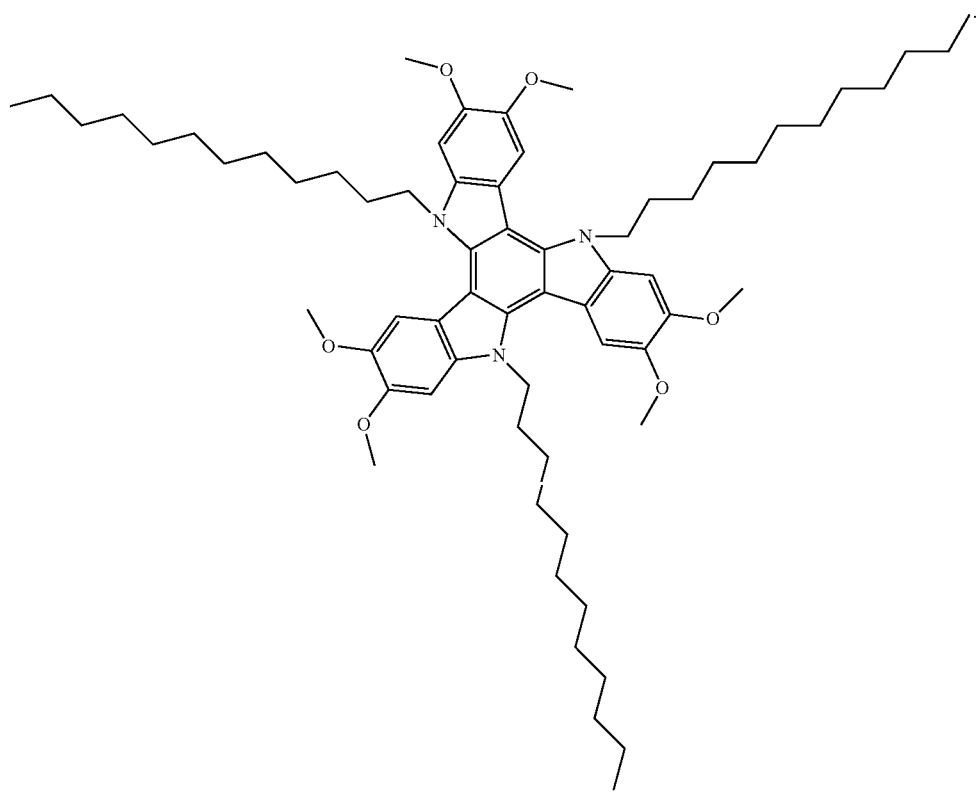

7. The chemical sensor of claim 1, wherein the HOMO level is greater than −4.9 eV.

8. The chemical sensor of claim 1, wherein the amine compound is an amine.

9. The chemical sensor of claim 1, wherein the electrical current is decreased for at least 5 minutes after exposure to the amine compound.

10. The chemical sensor of claim 1, wherein the amine compound adsorbs on the nanofiber mass for at least 5 minutes.

11. The chemical sensor of claim 1, wherein the nanofiber mass is deposited on the electrode.

12. The chemical sensor of claim 1, wherein the nanofiber mass is a film.

13. The chemical sensor of claim 1, wherein the chemical sensor detects the amine compound in a concentration of at least 1 ppm.

14. The chemical sensor of claim 1, wherein the chemical sensor is selective of the amine compound over other organic compounds.

15. The chemical sensor of claim 14, wherein the chemical sensor is selective by measuring a different electric current affected by the amine compound compared to the other organic compounds or by measuring a different length of time that the electric current is affected by the amine compound as compared to the other organic compounds.

16. The chemical sensor of claim 1, wherein the oxygen is free oxygen.

17. A method of detecting trace amine compounds, comprising:
 a) contacting the amine compound with a nanofiber mass of p-type nanofiber, said nanofibers having a HOMO level greater than −5.0 eV;
 b) measuring a change in electric current associated with the nanofiber mass before and after contacting the nanofiber mass with the amine compound.

18. The method of claim 17, wherein the nanofibers comprise a plurality of alkyl-substituted, carbazole-cornered, arylene-ethynylene tetracyclic macromolecules of formula 1:

Formula 1

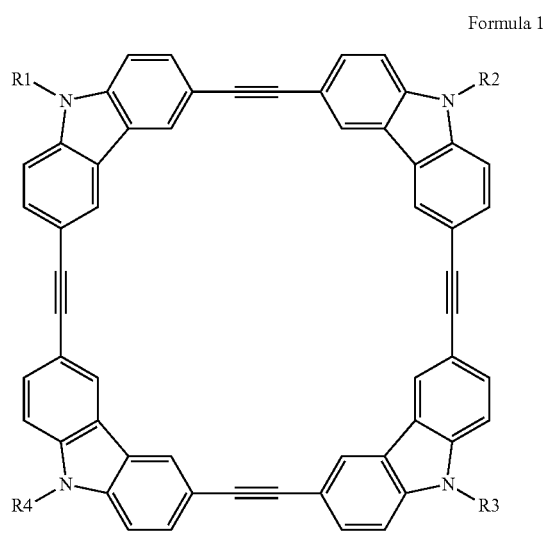

wherein R1-R4 are alkyl groups and wherein at least some of the macromolecules are cofacially stacked.

19. The method of claim 17, wherein the nanofibers comprise an indolocarbazole derivative.

20. The method of claim 19, wherein the indolocarbazole derivative is selected from the group consisting of

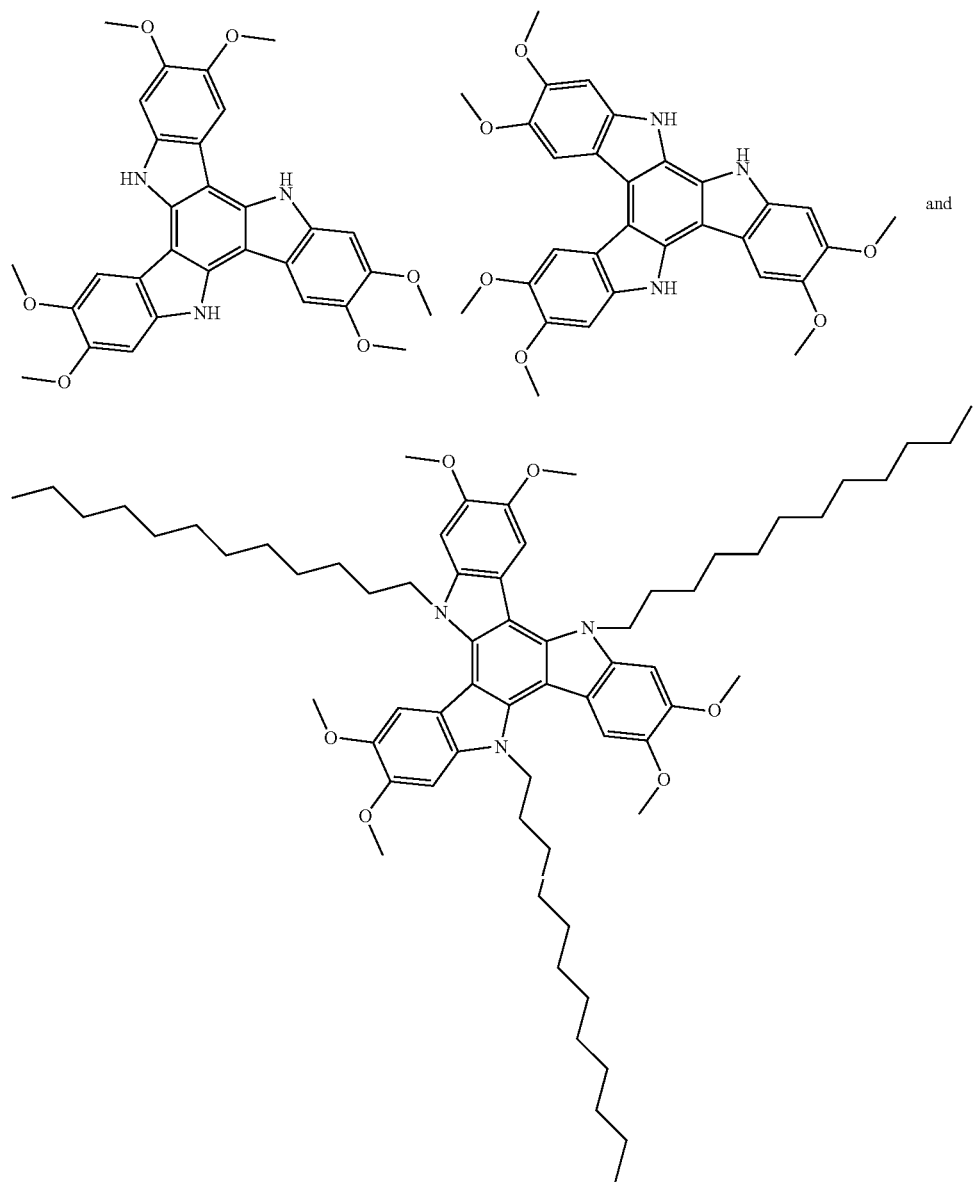

21. The method of claim 17, wherein the change in electric current decreases by at least 1% after the nanofiber mass is contacted with the amine compound.

22. The method of claim 17, wherein the amine compound is adsorbed on the nanofiber mass for at least 5 minutes.

23. The method of claim 17, wherein the change in electric current is measurable when the nanofiber mass contacts the amine compound in a concentration of at least 1 ppm.

24. The method of claim 17, further comprising differentiating between the amine compound and other organic compounds.

25. The method of claim 24, wherein the differentiating is by measuring a different electric current affected by the amine compound compared to the other organic compounds or by measuring a different length of time that the electric current is affected by the amine compound as compared to the other organic compounds.

26. The method of claim 17, wherein the method is used in the area selected from the group consisting of air pollution monitoring and controlling, food quality control, medical diagnosis, and security.

* * * * *